United States Patent [19]

Doiron et al.

[11] Patent Number: 5,330,465
[45] Date of Patent: * Jul. 19, 1994

[54] CONTINUOUS GRADIENT CYLINDRICAL DIFFUSION TIP FOR OPTICAL FIBERS AND METHOD FOR USING

[75] Inventors: Daniel R. Doiron, Santa Ynez; Hugh L. Narcisco, Jr.; Paul Paspa, both of Santa Barbara, all of Calif.

[73] Assignee: Laser Therapeutics, Inc., Buellton, Calif.

[ * ] Notice: The portion of the term of this patent subsequent to Mar. 23, 2010 has been disclaimed.

[21] Appl. No.: 969,413

[22] Filed: Oct. 30, 1992

Related U.S. Application Data

[62] Division of Ser. No. 799,047, Nov. 26, 1991, Pat. No. 5,196,005.

[51] Int. Cl.$^5$ .............................................. A61B 17/36
[52] U.S. Cl. ........................................ 606/7; 606/15; 606/16; 385/115
[58] Field of Search ................... 606/7, 15-19; 128/397, 398; 385/115-119

[56] References Cited

U.S. PATENT DOCUMENTS

| | | | |
|---|---|---|---|
| 4,660,925 | 4/1987 | McCaughan, Jr. | 606/15 X |
| 4,852,567 | 8/1989 | Sinofsky | 606/15 X |
| 4,860,743 | 8/1989 | Abela | 606/7 |
| 5,078,711 | 1/1992 | Kakami et al. | 606/15 X |
| 5,151,096 | 9/1992 | Khoury | 606/7 X |

*Primary Examiner*—Peter A. Aschenbrenner
*Attorney, Agent, or Firm*—Michael G. Petit

[57] ABSTRACT

A diffuser tip for a fiber optic or array of fibers having a proximal end which abuts against the tip of the fiber optic or array of fibers. The diffuser tip has a cylindrical center core of transparent elastomer which contains scattering centers embedded therein. The scattering centers are distributed within the core so that the concentration of scatterers increases continuously in a direction from the proximal end of the diffuser tip to the distal end of the diffuser tip.

3 Claims, 3 Drawing Sheets

CONTINUOUS GRADIENT CYLINDRICAL DIFFUSION TIP FOR OPTICAL FIBERS AND METHOD FOR USING

This application is a division of U.S. Ser. No. 07/799,047 filed Nov. 26, 1991 now U.S. Pat. No. 5,196,055.

BACKGROUND OF THE INVENTION

1. Field of the Invention

This invention relates generally to a means for cylindrically diffusing energy from an optical wave guide, and more particularly, to a cylindrical diffuser tip of an optical fiber useful for performing Photodynamic Therapy in the treatment of diseased tissue such as tumors, inducing hyperthermia or performing both percutaneous and intraoperative phototherapy of cardiovascular disease.

2. Reference to Co-Pending Patent Application

Reference is made to co-pending patent application U.S. Ser. No. 07/608,006 filed Nov. 1, 1990 entitled *Diffusion Tip for Optical Fibers* by two of the present inventors and having a common assignee with the present application.

3. Description of the Prior Art

Photodynamic treatment of tumors using hematoporphyrin derivatives requires that a tumor under treatment be irradiated with light usually around, but not limited to, a wavelength of 630 nanometers generally from a laser. A short time prior to irradiation, the patient is injected with a photo-sensitive compound which accumulates in the vascular stoma of the tumor and in cells. Subcutaneous tumors greater than 0.5 cm thick, also referred to herein as interstitial tumors, undergoing this treatment require the use of optical fibers to guide the light from the source to the treatment area. In many cases, the outlet termination of the fiber is inserted directly into the tumor. In other cases, where the tumor is located in passages, for example endobronchial tumors, the optical fiber termination is positioned intraluminally in close proximity to the tumor. Efforts have been directed in recent years to developing suitable fiber terminations for the delivery of a uniform, predictable dosage of effective irradiation of light to a large volume of tumor tissue.

Considerable light radiation must be transmitted to kill large tumor masses by photo irradiation and the required radiation can cause overheating, especially if it is concentrated in too small a region. This causes problems in delivering radiant energy out of the end of a normal blunt ended or flat cut optical fiber, making a small hot spot which may lead to excessive heating, carbonization and necrosis of the adjacent tissue making it opaque to transillumination. Thermal sources such as xenon arc lamps also pose difficulties in transmitting adequate radiation to deep-seated tumors because noncoherent sources cannot be coupled efficiently to reasonably small optical fibers for delivery to the tumor. Problems of distributing radiation uniformly throughout the region of a tumor to be killed are also formidable.

There are several ways that the cylindrical diffusion of radiant energy from an optical fiber core can be accomplished. One way is to choose a ratio of the indices of refraction between the outer cladding and the core region of the optical fiber so that internal reflection within the core region is substantially less than total. This causes light to enter the cladding. If scattering centers are present in the cladding the light can radiate outward to emerge through the (preferably transparent) cladding.

Another way is to alter the interface between the fiber optic core and cladding to increase side radiation. Texturing the outer surface of the core region to provide a ground glass effect is one method commonly used. Another is positioning or embedding light scattering elements such as tiny particles at the surface of the fiber optic core near the interface with the cladding. Light scattering particles can also be imbedded throughout the cladding to enhance the side delivery of radiation. Combinations of these measures are also possible.

For example, Chapman in United Kingdom patent GB2154761A (issued Sep. 11, 1985), which is incorporated herein by reference, describes an optical fiber for use in Photodynamic Therapy wherein the fiber comprises a central core material enveloped by a special two-layer cladding. The cladding comprises an inner cladding of a low refractive index material and an outer cladding. The fiber, being adapted to be coupled to a laser beam, has an output end portion which has a tapered core region which is surrounded by a diffusing medium. Light emerging from the tapered core region undergoes scattering.

In one preferred embodiment, Chapman's core is of circular cross section and the diameter of the core in the tapered region decreases uniformly to an end most point over a length of between 5 and 15 millimeters. In a further preferred embodiment, Chapman describes a diffusion medium comprising a transparent resin material, which contains fine particulate reflective or refractive matter.

Clark, in U.S. Pat. No. 4,336,809 (issued Jun. 29, 1982) describes a tissue photo irradiation system for use with hematoporphyrin dyes and derivatives thereof. In Clark's system he describes the use of an optical needle which serves as a linear radiator or a cylindrical diffuser and which can be coupled to an optical fiber by means of a conventional optical coupler. Clark's needle includes a fiber optic core that is generally internally reflecting. The core is surrounded by a cladding as generally known; but in an end region a different cladding surrounds the core to make it into a radiator instead of an internally reflecting transmitter. When the cladding contains scatterers, the "needle" or diffusion tip comprises a transparent core surrounded by a scattering layer in which the concentration of scatterers is homogeneous along its length.

Production of a controllable level of temperature elevation or hyperthermia at pre-selected locations in volumes of tissue has been found to be of significant therapeutic value in the treatment of patients with cancer. In particular, hyperthermia may, in some cases, have a synergistic effect when used in conjunction with Photodynamic Therapy for treating tumors or performing angioplasty. At the high power levels required for hyperthermia or hyperthermia plus Photodynamic Therapy, high peak intensities or hot spots can lead to excessively high temperatures causing unintentional non-selective tissue damage. It is, therefore, desirable to distribute the illuminating energy evenly within the target volume to achieve uniform temperature distributions.

The present fiber optic cylindrical diffuser tip technology is limited in clinical applications due to the following:

a) The underlying fiber optic is weakened by mechanical processing during manufacturing of the cylindrical diffusing tip;

b) The weakened fiber optic limits the flexibility of the finished cylinder diffuser to the point of sole quasi-rigid usage (very limited endoscopic use);

c) Output sensitivity of prior art cylindrical diffuser tips to input beam convergence causes extreme variability in the output intensity distribution.

d) A non-uniform output intensity distribution makes treatment dosimetry uncertain and clinical results inconsistent; It is desirable, therefore, to provide a cylindrical diffuser for use as a termination on an optical fiber which overcomes most or all of the limitations stated above.

McCaughan, Jr., in U.S. Pat. No. 4,660,925 (Issued Apr. 28, 1987) incorporated herein by reference, describes a cylindrical diffuser tip that overcomes some of the problems with prior art diffuser tips. McCaughan Jr. suggests (column 4, lines 48-62) providing a tip surrounding the core of an optical fiber, the tip containing a gradient of scatterers which increases logarithmically in concentration along the fiber axis in a direction toward the polished tip of the optical fiber. To accomplish this, McCaughan, Jr. teaches a method for making such a tip comprising the steps of exposing the core of an optical fiber near its tip, polishing the exposed core and repeatedly dipping the tip in a medium containing different concentrations of scatterers to allegedly increase the concentration of scatterer along the length of the exposed core. The polished tip of the core (column 5, lines 47-49) region is cleaned of scattering medium upon removal from the dipping vessel. The word "allegedly" is used above because such a method of repetitive coating followed by the step underlined above is inoperable to produce a longitudinal gradient of scatterer in a diffuser tip. This method produces a radial gradient in scatterer concentration which varies radially with distance from the fiber core axis. Even if this method could, by further experimentation, be made operable, such a method would provide, at best, a discrete, step-wise concentration gradient which would only approximate a logarithmic gradient in the limit of infinite coatings.

Two of the present inventors (D. D., H. N., Jr.), in co-pending application U.S. Ser. No. 07/608,006 filed Nov. 1, 1990 entitled: Diffusion Tip for Optical Fibers, suggest a composite tip comprised of laminated layers or "plugs" of elastomer, each plug having a higher concentration of scatterer embedded therein than the preceding layer as one moves away from the optical fiber tip along the fiber axis. While such a tip is an improvement over McCaughan, Jr. in that it provides a step-wise concentration gradient in a longitudinal direction but not a radial direction as with McCaughan (i.e.: no dipping of the exposed core is involved), and only approximates a continuous concentration gradient but does not produce a gradient that is optimal.

SUMMARY OF THE INVENTION

One object of this invention is to provide a diffusion tip for an optical fiber having a longitudinal continuous concentration gradient of scattering centers throughout its length which enables the cylindrical diffusion of radiant energy from the fiber uniformly along the length of the tip.

Another object of this invention is to provide a cylindrical diffusion tip for an optical fiber which is flexible.

Yet a further object of this invention is to provide a diffuser tip for an optical fiber which tip avoids high intensity non-uniform distribution of light energy commonly referred to as hot spots caused by silica fiber core manipulation or discrete scatterer concentration variations.

Yet a further object is to provide an optical fiber cylindrical diffusion tip for use in Photodynamic Therapy treatment of tumors that efficiently and uniformly cylindrically diffuses transmitted light and which diffuser tip has a maximum diameter substantially the same as that of the fiber incorporated therein.

Still another object of this invention is to provide an optical fiber diffuser tip which is useful for the treatment of atheromas in angioplasty.

Yet another object of this invention is to provide a terminal diffuser tip for an optical fiber useful for inducing hyperthermia in selected target tissue.

A further advantage of the termination tip of the present invention is that it is input mode independent. That is, the distribution of light out of the diffuser is independent of the coupling mode.

Yet another object of this invention is to provide a guidewire compatible terminal diffuser tip for an optical fiber to create a uniform cylindrical distribution of light for use in tubular structures such as blood vessels, ureters, urethras, the colon and so forth.

Accordingly, the present invention teaches the use of a diffusion tip in which a conventional optical fiber (with cladding and jacket) is terminated by abutting it with a elastomeric fiber core having an outer diameter slightly greater than that of the optical fiber's core yet less than or equal to the outer diameter of the optical fiber's jacket. The elastomeric fiber core comprises a continuous gradient along the longitudinal axis of scattering centers embedded in an optically transparent elastomer substrate comprising preferably transparent silicone wherein the light scattering centers continuously increase in concentration along the diffuser tip core axis in a direction away from the optical fiber face. In one embodiment, an air space is disposed between the tip of the optical fiber core and the core of the diffuser tip. This geometry allows high power usage by coupling substantially the same amount of power as the directly contacting embodiments (FIGS. 2-5) while reducing the power density considerably. The tip produces a predictable and repeatable output distribution pattern which can be tailored to any application.

A DESCRIPTION OF THE PREFERRED EMBODIMENT

Figure 1:
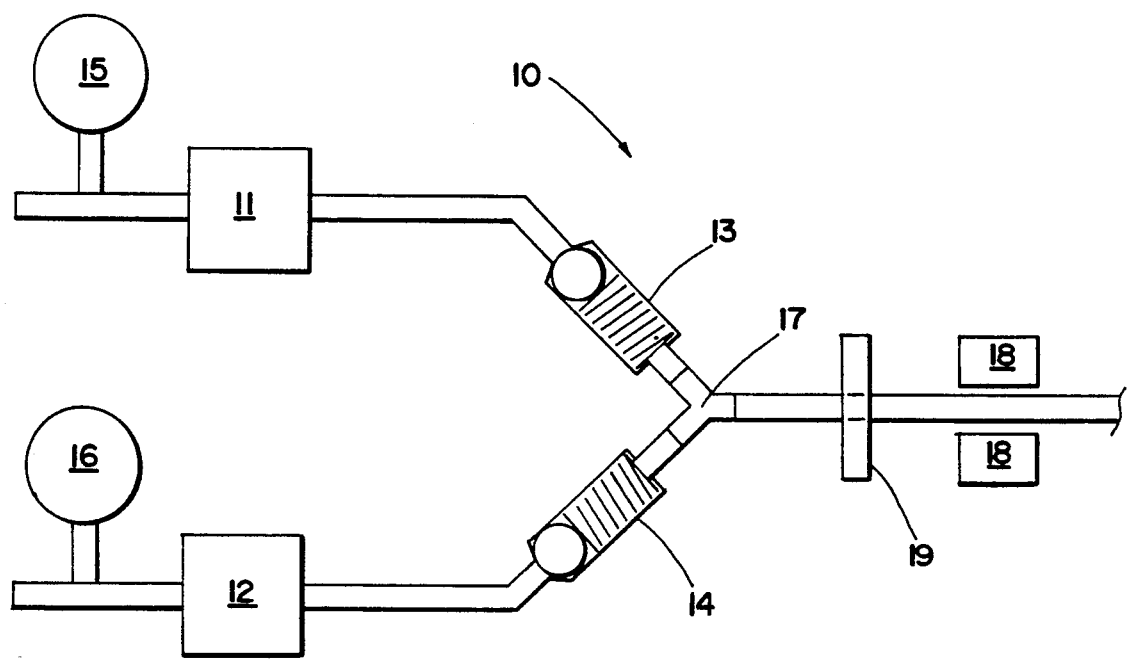
FIG. 1 is a schematic view of a multichannel single head extruder useful for making an extruded diffuser tip core having a continuous controllable gradient of scatterers along its length.

Extrusion processes for forming cylindrical articles are well known in the art. Extruders are also commonly used to produce tubing as, for example, shown in U.S. Pat. No. 4,053,274, the specification of which is incorporated herein by reference. An extrusion apparatus adapted to produce a concentration gradient of scattering centers in the elastomer substrate is shown in FIG. 1. To produce an elastomeric core for the tip having the desired gradient (which may or may not be linear) of light scatterers embedded therein, a dual injector system (or multiple injector system) generally indicated at numeral 10 in FIG. 1 is employed. A first injector 11 contains a mixture of highly concentrated scatterers in the elastomer base. A second injector 12 contains a low concentration of scatterers in elastomer or elastomer alone. The two mixtures are forced through check values 13 and 14 respectively by pumps 15 and 16 and into a mixer 17 where they are combined in volumes predetermined to produce the desired final concentration of scatterers in the core 24 which emerges from the extruder 10 through one or more orifices (dotted lines) of an extrusion die 19. It is preferable to have the volume of the mixer 17 less than or equal to the volume of the orifice(s) in the extruder die 19 to enable greater control over the concentration of light scattering centers in the extruded fiber.

While the dual injection and mixing processes are occurring, an on-line detection system 18 monitors the concentration of light scatterers in the core as the core 24 is extruded. This information is relayed to a controller system (not shown) which regulates the flow from each injector to produce the optimum concentration gradient. Once determined, this optimum concentration gradient can be reproduced by programming the appropriate algorithms into a controller which independently regulates injectors 11 and 12.

The extruded core 24 comprising an extrudable transparent elastomer with the desired concentration gradient of scattering centers embedded therein is cured and forced into a plastic tube, the inner diameter of the tube being equal to or greater than the outer diameter of the optical fiber to which the tip is to be attached.

Figure 2:
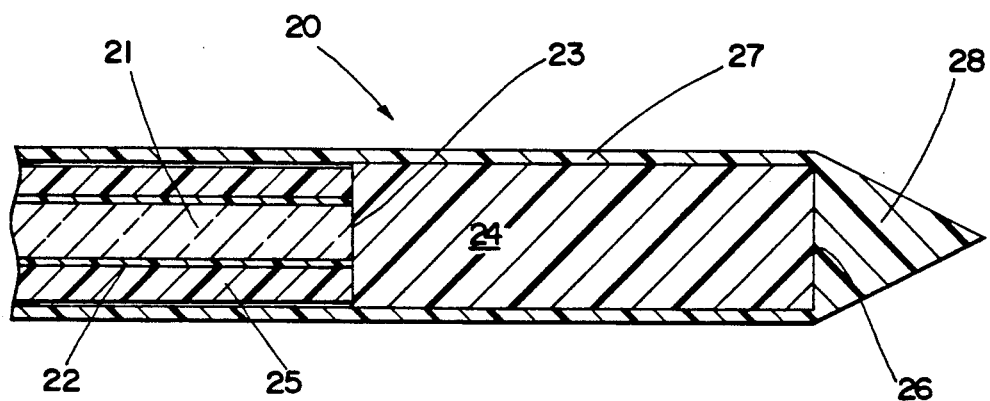
FIG. 2 is a longitudinal cross-sectional view of a first preferred embodiment of the continuous gradient diffusion tip showing a pointed tip to facilitate insertion through tissue.

A first preferred embodiment of the optical fiber cylindrical diffuser tip of the present invention is indicated generally at 20 in FIG. 2. A standard optical fiber consisting of a core 21, cladding 22 and jacket 25 has a blunt distal end indicated at 23. The core of the diffuser tip 24 is preferably extruded from transparent silicone and has a proximal end which is recessed to accommodate the distal end 23 of an optical fiber and a distal end 26. In practice, the outer diameter of the core (24) of the cylindrical diffuser tip 20 is greater than the outer diameter of the optical fiber core 21 plus cladding 22 plus jacket 25. The diffuser tip 20 may be any length but is preferably between 0.5 and 5 cm for Photodynamic Therapy irradiation of tumors, phototherapy of cardiovascular disease, and laser induced hyperthermia of tumors.

After the silicone core 24 of the diffuser tip 20 is affixed to the optical fiber terminus 23 a plastic tube 27 is slid over the diffuser tip core 24 and optical fiber Jacket 25 to provide a secure bond therebetween. The diffuser tip 20 thus obtained may be extremely flexible without the plastic tube 27. In practice, it is desirable to stiffen the fiber by the insertion of an optically transparent tubing 27 over the silicone core of the diffuser tip. A pointed tip 28 may be affixed to the tube 27 facilitate interstitial insertion.

The choice of material and wall thickness of the tubing 27 will ultimately determine the flexibility of the diffuser tip. The distribution of scattered light emanating from the silicone core of the diffuser tip can be controlled by varying the concentration gradient of scatterer in the silicone. If the concentration of scatterer is moderate and homogeneous along the length of the core of the diffuser tip, a linear intensity distribution with negative slope results. If the concentration increases exponentially along the core the distribution of radiant energy emanating radially from the core will be linear with a zero slope as is desired. Other gradients can, of course, be used to generate other desired distributions of light.

Figure 3:
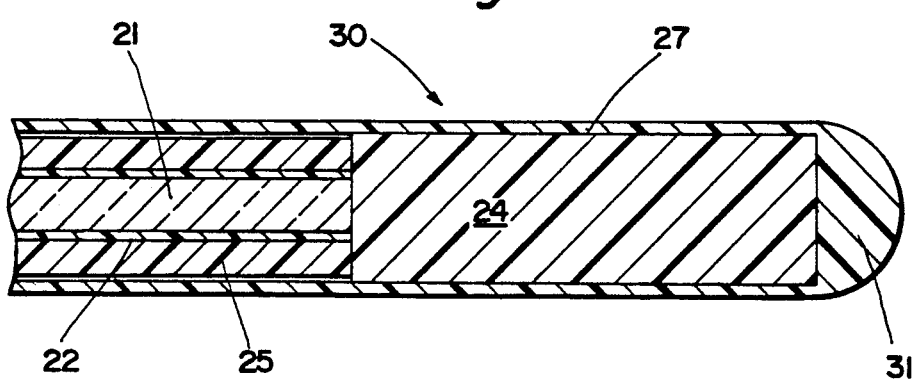
FIG. 3 shows a longitudinal cross-sectional view of a second preferred embodiment of the diffusion tip having a rounded tip useful for intraluminal illumination of a tubular member.

FIG. 3 shows a cylindrical diffuser tip 30 according to the present invention in which the terminal tip 31 of the diffuser is rounded to enable insertion into the lumen of tubular tissue without the danger of puncturing the wall of such tissue. This tip is useful, for example, for illuminating tissues along the wall of the esophagus, bronchl, urethra or blood vessels.

Figure 4:
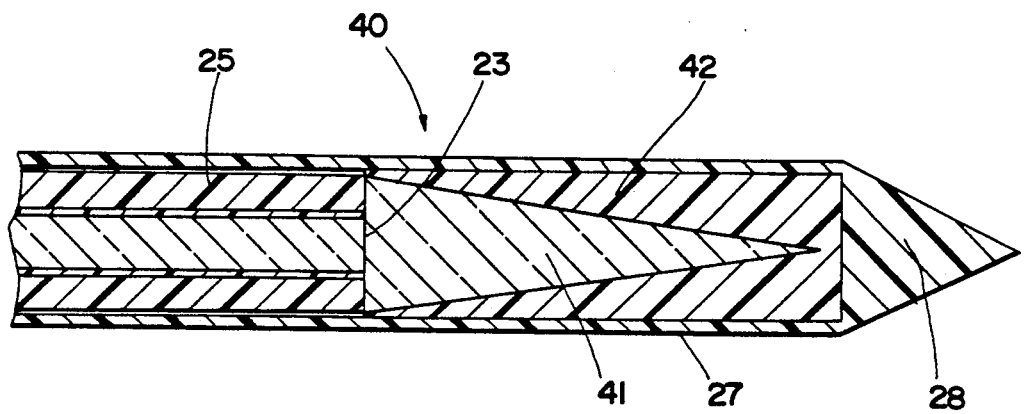
FIG. 4 is a longitudinal cross-sectional view of a third preferred embodiment of a diffuser tip in which the silicone tip is molded onto the optical fiber in two stages; one stage adding a conical transparent silicone core, the second stage adding a surrounding core containing scatterers arranged in a continuous gradient along the length of the diffuser.

Turning now to FIG. 4 a diffuser tip, generally indicated at 40, for use in irradiating interstitial tumors, is similar to the diffuser tip 20 in that it has a sharp pointed tip 28 enabling the tip to be pushed into and through tissue with or without the aid of a cannula. For interstitial use, it is desirable that the tip have as small an outer diameter as possible to facilitate penetration of the tumor. This interstitial cylindrical diffusion tip has a core consisting of a transparent conical portion 41 and a scattering portion 42. The tip 40 is made by first bonding the conical portion 41 of the core to the optical fiber terminus 23. Core scattering portion 42 is made by extruding core 24 (not indicated in FIG. 4) as described earlier and removing a conical section therefrom to accommodate the conical portion 41. Scattering section 42 is then bonded to transparent conical portion 41 and allowed to cure. Once cured, the tubular tip jacket 27 may be slipped over the core 42 and fiber jacket 25 and pushed up the fiber beyond the optical fiber's terminus 23. The conical translucent or opaque piercing tip 28 is then pressed into the uncured scattering layer and the assembly is allowed to cure. This tip is particularly useful for inducing hyperthermia in tissue surrounding the tip.

Figure 5:
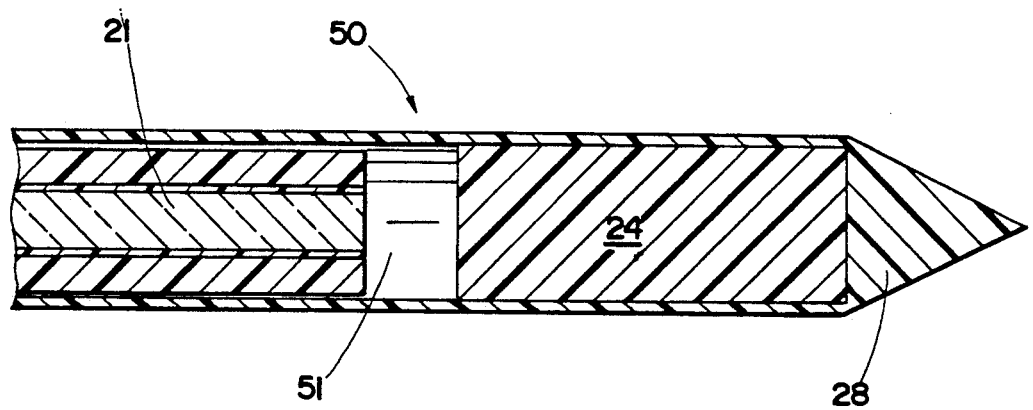
FIG. 5 is similar to FIG. 2 except that the continuous gradient silicone diffuser tip is separated from the tip of the optical fiber by a space which may contain air, gas, or liquid for high power application.

FIG. 5 shows yet another cylindrical diffuser tip, indicated at numeral 50 for irradiating interstitially. In this embodiment, a gap 51 between the fiber optic terminus and the proximal end of the silicone/scatterer core 24 of the diffuser tip 50 is incorporated. The gap 51 may be filled with air, gas, or liquid. The gap 51 provides space for a coupling fluid (gas or liquid) which reduces light energy density from the fiber optic by allowing the output to expand substantially prior to coupling to the core 24, thus the overall energy remains virtually unchanged. This configuration 50 allows for much higher power handling capabilities.

Figure 6:
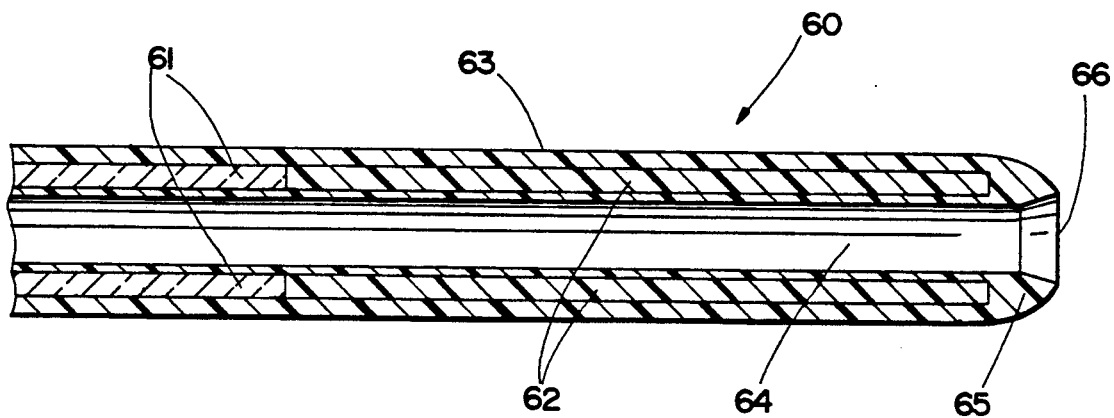
FIG. 6 shows a longitudinal cross-sectional view of a continuous gradient cylindrical diffuser tip of the present invention having a guidewire compatible lumen forming a central axis for use in intraluminal applications such as angioplasty.

FIG. 6 shows a continuous gradient diffuser tip according to the present invention adapted for use with a guidewire-compatible angioplasty catheter or the like for irradiating target tissue on the wall Of tubular tissue. The diffuser tip 60 has a proximal end which abuts against the annular array of fiber optics 61 of an angioplasty catheter and a distal end 65. The annular core 61 of the catheter usually consists of a tubular bundle of optical fibers disposed around a central lumen 64. The central lumen 64 of the catheter is sized to accommodate a guidewire therewithin. The core 62 of the diffuser tip is extruded in the manner described earlier except that a mandrel (not shown) is disposed centrally within the orifice of the extruder die 19 (FIG. 1) in a manner well known in the art for extruding tubular members. The diffuser tip core 62 formed and described above has a continuous gradient of light scattering centers embedded therein which increase continuously in concentration from the proximal end to the distal end. The diffuser tip 60 may be inserted over a guidewire (not shown) by means of the guidewire portal 66.

It is important that the silicone used in the diffuser tip core be free of bubbles. This may be facilitated by applying a vacuum to the uncured silicone prior to use. Optical quality silicone, available from McGhan NuSil Corporation, Carpinteria, Calif., Catalog No. CF1-6755 is suitable for the construction of such tips.

Figure 7:
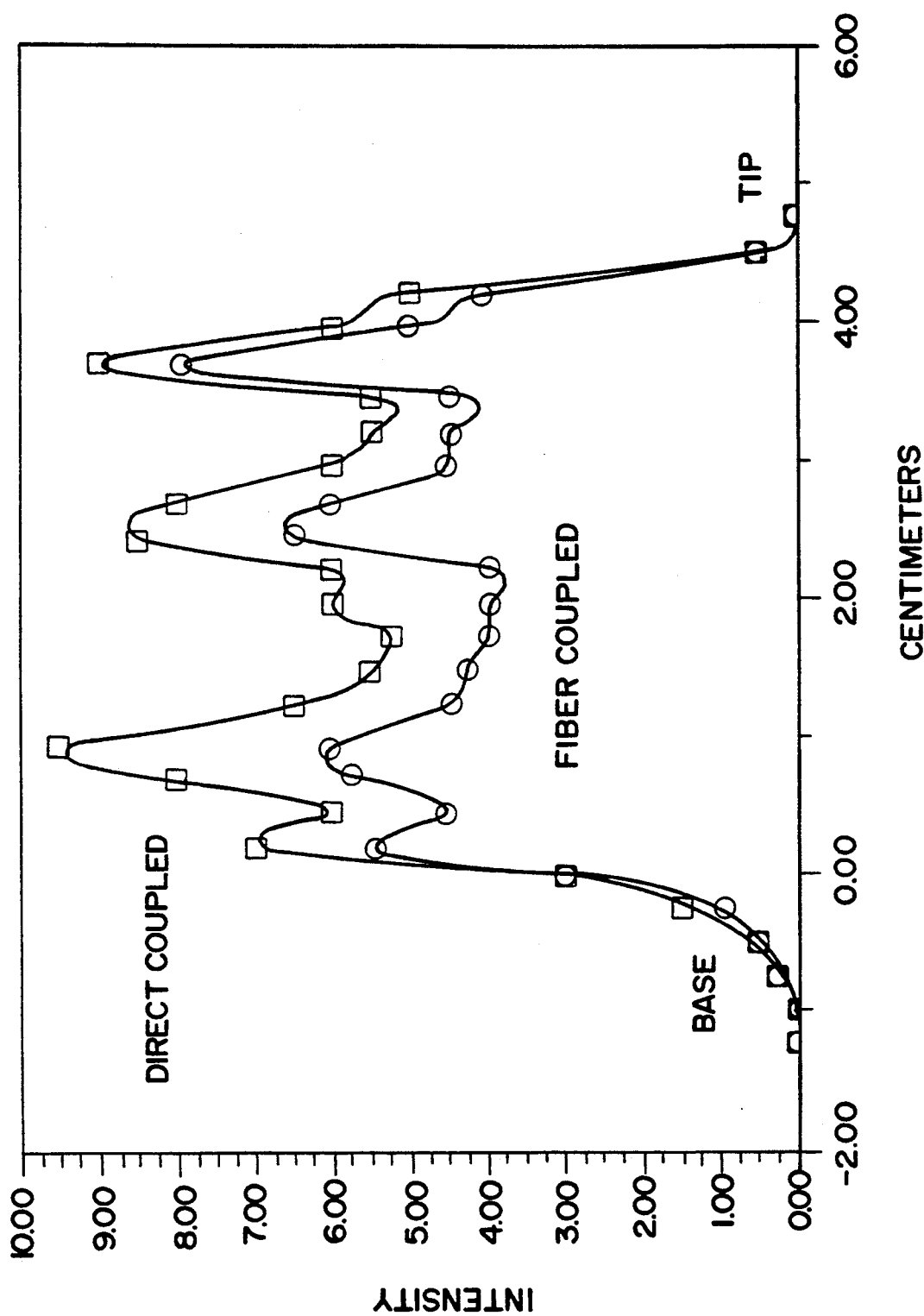
FIG. 7 shows the insensitivity of the distribution of light emanating from the fiber optic diffuser tip according to the present invention for two different modes of coupling light into the optical fiber.

As mentioned earlier, sensitivity of the output of prior art cylindrical diffuser tips to input beam divergence causes extreme variability in the output intensity distribution. The distribution of light emanating from each of the embodiment of the diffuser tip of the present invention is substantially independent of input coupling mode as shown in FIG. 7.

The foregoing embodiments of the optical fiber cylindrical diffuser tip are offered by means of example, The invention should not be limited to the specific embodiments presented herein but only by the scope of the claims appended hereto.

What is claimed is:

1. A method for administering photodynamic therapeutic treatment to tumors comprising the steps of:
   (a) introducing a suitable photosensitive molecule into or around the tumor; and
   (b) photoirradiating said photosensitive molecules by means of a diffuser tip to deliver an amount of light energy sufficient to effect the destruction of the tumor cells;

wherein said diffuser tip has a proximal end which abuts against the tip of an optical fiber or array of fibers and a distal end, said diffuser tip comprising a cylindrical central core of an optically transparent elastomer, said core containing light scattering centers embedded therein, said light scattering centers being distributed within the core so that the concentration of light scattering centers increases continuously in a direction from the proximal end of the diffuser tip to the distal end of the diffuser tip.

2. A method for treating atherosclerotic plaque in the wall of a blood vessel comprising the steps of:
   (a) introducing a photosensitive compound into the plaque, said photosensitive compound being capable of being activated by photoirradiation and thereafter capable of destroying atherosclerotic plaque tissue; and
   (b) insertion of an optical fiber into the blood vessel, said fiber having a light diffuser tip; and
   (c) irradiating the plaque with light of a wavelength suitable for photoactivating said photosensitive compound; and
   (d) delivering sufficient light energy to the photosensitive compound to cause necrosis of the atherosclerotic plaque tissue in the wall of the blood vessel, wherein said diffuser tip has a proximal end which abuts against the tip of an optical fiber or array of fibers and a distal end, said diffuser tip comprising a cylindrical central core of a substantially optically transparent elastomer, said core containing light scattering centers embedded therein, said light scattering centers being distributed within the core so that the concentration of light scattering centers increases continuously in a direction from the proximal end of the diffuser tip to the distal end of the diffuser tip.

3. A method inducing hyperthermia in a target tissue comprising the steps of:
   (a) inserting a diffuser tip into said target tissue;
   (b) irradiating the target tissue with light emanating from said diffuser tip until the desired hyperthermia is induced in the target tissue, wherein said diffuser tip has a proximal end which abuts against the tip of an optical fiber or array of fibers and a distal end, said diffuser tip comprising a cylindrical central core of a substantially optically transparent elastomer, said core containing light scattering centers embedded therein, said light scattering centers being distributed within the core so that the concentration of light scattering centers increases continuously in a direction from the proximal end of the diffuser tip to the distal ned of the diffuser tip.

* * * * *